United States Patent [19]

Seitz et al.

[11] Patent Number: 4,940,780

[45] Date of Patent: Jul. 10, 1990

[54] BASICALLY SUBSTITUTED PHENYLACETONITRILES, THEIR PREPARATION AND DRUGS CONTAINING THESE COMPOUNDS

[75] Inventors: Werner Seitz, Plankstadt; Liliane Unger, Ludwigshafen; Manfred Raschack, Weisenheim am Sand; Verena Baldinger, Heidelberg; Klaus Ruebsmen, Neustadt; Josef Gries, Wachenheim, all of Fed. Rep. of Germany

[73] Assignee: BASF Aktiengesellschaft, Ludwigshafen, Fed. Rep. of Germany

[21] Appl. No.: 130,954

[22] Filed: Dec. 10, 1987

[30] Foreign Application Priority Data

Dec. 11, 1986 [DE] Fed. Rep. of Germany ....... 3642331

[51] Int. Cl.$^5$ ............................................ C07D 121/75
[52] U.S. Cl. .................................... 558/388; 558/430
[58] Field of Search ......................... 558/388; 574/646

[56] References Cited

U.S. PATENT DOCUMENTS

| 3,440,302 | 4/1969 | Speier et al. | 260/825 |
| 4,003,914 | 1/1977 | Ramuz | 260/327 M |
| 4,038,407 | 7/1977 | Eberlein et al. | 424/270 |
| 4,593,042 | 6/1986 | Liang | 514/523 |
| 4,610,990 | 9/1986 | Esanu | 514/302 |
| 4,659,719 | 4/1987 | Esanu | 514/302 |

FOREIGN PATENT DOCUMENTS

| 916157 | 12/1972 | Canada . |
| 0157206 | 9/1985 | European Pat. Off. . |
| 0064158 | 3/1986 | European Pat. Off. . |
| 0180810 | 5/1986 | European Pat. Off. . |
| 0147707 | 3/1987 | European Pat. Off. . |
| 1493904 | 3/1962 | Fed. Rep. of Germany . |
| 1593921 | 10/1970 | Fed. Rep. of Germany . |
| 1643429 | 1/1971 | Fed. Rep. of Germany . |
| 2460593 | 7/1975 | Fed. Rep. of Germany . |
| 2509797 | 9/1976 | Fed. Rep. of Germany . |
| 3537715 | 10/1985 | Fed. Rep. of Germany . |
| 3538063 | 10/1985 | Fed. Rep. of Germany . |
| 1544810 | 5/1986 | Fed. Rep. of Germany . |
| 0000304 | 1/1984 | Japan . |
| 0146001 | 7/1984 | Japan . |
| 1090609 | 1/1967 | United Kingdom . |
| 1202750 | 8/1970 | United Kingdom . |

OTHER PUBLICATIONS

"Drugs of Today", vol. 20, No. 2, (1984), pp. 69–90.
"Drug Research", 31(I), 5 (1981), pp. 773–780.

Primary Examiner—William R. Dixon, Jr.
Assistant Examiner—James M. Hunter, Jr.
Attorney, Agent, or Firm—Keil & Weinkauf

[57] ABSTRACT

Basically substituted phenylacetonitriles

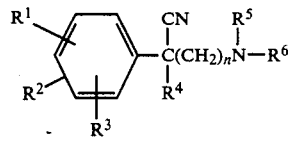

where $R^1$ to $R^6$ and n have the meanings stated in the description, and their preparation are described. The compounds are useful for the treatment of disorders.

15 Claims, No Drawings

BASICALLY SUBSTITUTED PHENYLACETONITRILES, THEIR PREPARATION AND DRUGS CONTAINING THESE COMPOUNDS

The present invention relates to novel basically substituted phenylacetonitriles, their preparation and drugs which contain these substances.

German Patent Nos. 1,544,810 and 1,493,904, German Laid-Open Applications Nos. DOS 1,593,921, DOS 1,643,429, DOS 3,538,063 and DOS 3,537,715, European Laid-Open Application Nos. 147,707, 64,158, 157,206 and 180,810 and Japanese Preliminary Published Application Nos. 146,001 (=Derwent No. 86-078808/12) and 304 (=Derwent No. 85-226650/37) and U.S. Pat. No. 4,593,042 describe basically substituted phenylacetonitriles. From this class of compounds, verapamil (X=H) and gallopamil (X=OCH$_3$)

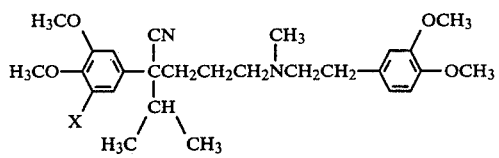

has proven useful in the therapy of coronary heart diseases and of high blood pressure, owing to their calcium-antagonistic action.

For the verapamil molecule, relationships between the chemical structure and biological action have been described in various publications (Arzneim. Forsch./Drug Res. 5 (1981), 773).

On the basis of these structure/activity considerations and experimental work, Mannhold [Drugs of Today 20 (2) (1984), 69–90] has shown that both aryl radicals of the verapamil molecule are essential to the biological activity.

The compounds mentioned in the above patents are all distinguished by the fact that the basic nitrogen is substituted by a low molecular weight alkyl group and, at the right of the nitrogen, by an aralkyl group. The basic nitrogen and the aryl radical are separated by two or more carbon atoms, which may furthermore be part of a partially hydrogenated bicyclic aromatic or heteroaromatic substituent (e.g. a tetrahydronachthyl or isochroman ring) or part of a ring (e.g. a piperidine ring).

More far reaching modifications of verapamil, as described in, for example, German Laid-Open Applications Nos. DOS 2,509,797 and DOS 2,460,593, also contain the phenethylamine side chain as an essential structural element.

We have found that novel basically substituted phenylacetonitriles of the formula I

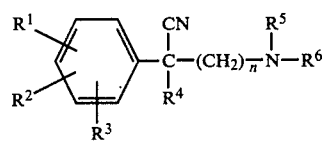

where $R^1$, $R^2$ and $R^3$ are identical or different and are each hydrogen, halogen, trifluoromethyl, $C_1$–$C_4$-alkyl, nitro or $C_1$–$C_4$-alkoxy, and two radicals in adjacent positions may furthermore together form a methylenedioxy, ethylenedioxy, 1,3-dioxatetramethylene, propylene or butylene group, $R^4$ is saturated or unsaturated alkyl or is cycloalkyl or phenyl, $R^5$ is hydrogen or $C_1$–$C_4$-alkyl, $R^6$ is a saturated or unsaturated hydrocarbon radical of 6 to 15 carbon atoms which may contain a ring, and n is 2, 3 or 4, and their antipodes and salts with physiologically tolerated acids are highly active, despite the lack of the aryl radical in the phenalkyl side chain.

Preferred halogen atoms $R^1$, $R^2$ and $R^3$ are fluorine and chlorine. Preferred alkyl and alkoxy groups $R^1$, $R^2$ and $R^3$ are those of 1 or 2 carbon atoms. Preferred nitro and trifluoromethyl compounds are those having one nitro or trifluoromethyl group. $R^4$ is preferably of up to 6 carbon atoms.

The following compounds are particularly interesting:

5-[N-methyl-N-(n-octyl)]-amino-2-(3,4,5-trimethoxyphenyl)-2-isopropylvaleronitrile and its enantiomers, 5-[N-methyl-N-(n-hexyl)]-amino-2-(3,4,5-trimethoxyphenyl)-2-isopropylvaleronitrile and its enantiomers, 5-[N-methyl-N-2-cyclohexylethyl)]-amino-2-(3,4,5-trimethoxyphenyl)-2-isopropylvaleronitrile and its enantiomers, 5-[N-methyl-N-(2-cyclohexylethyl)]-amino-2-phenyl-2-isopropylvaleronitrile and its enantiomers, 5-{N-methyl-N-[2-cyclohexen-1-yl)ethyl]}-amino-2-(3,4,5-trimethoxyphenyl)-2-isopropylvaleronitrile and its enantiomers, 5-{N-methyl-N-[2-(cyclohexen-1-yl)ethyl]}-amino-2-phenyl-2-isopropylvaleronitrile and its enantiomers.

Examples of suitable physiologically tolerated acids are hydrochloric acid, hydrobromic acid, sulfuric acid, phosphoric acid, acetic acid, maleic acid, lactic acid, tartaric acid, citric acid and fumaric acid.

The novel compounds possess one or more asymmetric carbon atoms and therefore occur in various enantiomeric forms. Consequently, the compounds I can be prepared either in optically active forms or as racemic mixtures. The racemates of the compounds I can be resolved into their optical antipodes by a conventional method, for example by separation (fractional crystallization, column chromatography) of the diastereomeric salts. The latter can be prepared by reacting the compounds I with chiral acids. The enantiomeric forms can also be obtained by using optically active starting compounds.

The novel compounds are prepared by a method in which (a) a phenylacetonitrile of the formula II

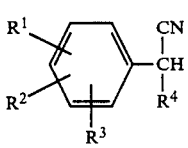

where $R^1$ to $R^4$ have the stated meanings, is reacted with an amine of the formula III

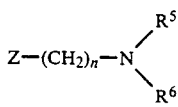

where $R^5$, $R^6$ and n have the stated meanings and Z is a leaving group, or (b) a basically substituted phenylacetonitrile of the formula IV

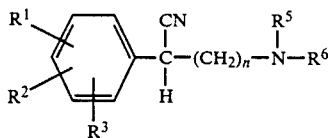

where $R^1$ to $R^3$, $R^5$, $R^6$ and n have the stated meanings, is reacted with a compound of the formula V $$R^4\text{-}Z \qquad (V)$$

where $R^4$ and Z have the above meanings, or (c) a phenylacetonitrile of the formula VI

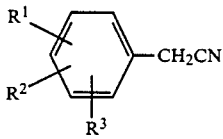

where $R^1$ to $R^3$ have the stated meanings, is reacted with an amine of the formula III and a compound of the formula V, or (d) a phenylacetonitrile of the formula VII

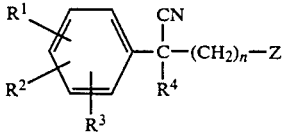

where $R^1$ to $R^4$, n and Z have the abovementioned meanings, is reacted with an alkylamine of the formula VIII

where $R^5$ and $R^6$ have the above meanings, or (e) a phenylacetonitrile of the formula IX

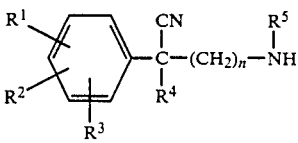

or of the formula X

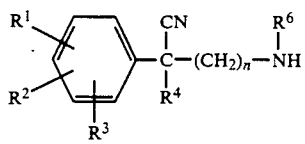

where $R^1$ to $R^6$ and n have the meanings described, is reacted with a compound of the formula XI or XII, respectively, XI $R^6$-Z or XII $R^5$-Z where $R^5$, $R^6$ and Z have the abovementioned meanings (except that $R^5$ must not be H), or (f) where $R^5$ and $R^6$ contain a $CH_2$ group bonded to the nitrogen atom, a phenylacetonitrile of the formula IX or X is reacted with an aldehyde of the formula XIII or XIV, respectively, XIII $R^7$—CHO or XIV $R^8$—CHO where $R^7$ and $R^8$ are defined so that $R^7$—$CH_2$ is the same as $R^5$ and $R^8$—$CH_2$ is the same as $R^6$, under reductive conditions, or (g) an aldehyde of the formula XV

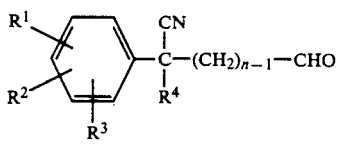

where $R^1$ to $R^4$ and n have the same meanings as above, is reacted with an alkylamine of the formula VIII under reductive conditions, or (h) a dinitrile of the formula XVI

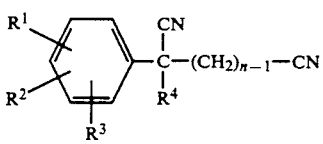

where $R^1$ to $R^4$ and n have the same meanings as above, is reduced in the presence of an alkylamine of the formula VIII, or (i) a nitrile of the formula XVII or XVIII $R^7$—CN XVII or $R^8$—CN XVIII where $R^7$ and $R^8$ are as defined above and $R^7$ cannot be hydrogen, is hydrogenated with a phenylacetonitrile of the formula IX or X, or (k) where $R^6$ contains a $CH_2$ group bonded to the nitrogen atom, a phenylacetonitrile of the formula XIX

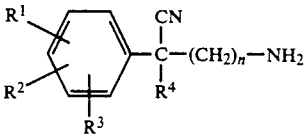

where $R^1$ to $R^4$ and n have the same meanings as above, is hydrogenated in the presence of a nitrile of the formula XVIII, and, if desired, a $C_1$-$C_4$-alkyl group is introduced into the resulting compound if $R^5$ is hydrogen, and, if required, the compound is then converted to its salts with physiologically tolerated acids.

Reaction (a) can be carried out, for example, by metallizing a CH-acidic phenylacetonitrile of the formula II in an inert solvent with a base and then reacting the product with a compound of the formula III. In another possible procedure, the base may be added to a solution of compounds of the formulae II and III.

Suitable bases are alkali metal hydrides, alkali metal hydroxides, alkali metal alcoholates and alkali metal amides and organometallic compounds. Sodium amide powder and suspension, potassium hydroxide powder, butyllithium and lithiumdiisopropylamide are preferably used.

Suitable solvents for the reaction are aromatic and aliphatic hydrocarbons, although fairly high boiling aliphatic ethers and dipolar aprotic solvents are also useful. Toluene is preferably employed.

Reaction (a) can also be carried out under phase transfer catalysis. The catalysts used are quaternary ammonium and phosphonium salts, crown ethers, polyethylene glycol dialkyl ethers (eg. PEG 600 dibutyl ether) and tris-(3,6-dioxaheptyl)-amine (TDA-1).

The reaction temperatures depend on the bases used; for example, the reaction is carried out at from 0° to −100° C. in the case of butyllithium and preferably at from 50° to 150° C. when sodium amide is used.

Examples of suitable leaving groups Z are chlorine, bromine, sulfuric esters, tosylates, mesylates and triflates.

The conversion of compounds of the formula IV into the novel compounds process (b) is carried out similarly to process (a).

Suitable reactants are alkane derivatives of the formula V, the leaving group Z having the same meanings as above.

In process (c), the compounds III, V and VI may be added in any order, and intermediates need not be isolated.

Reaction (d) is carried out by simply heating the reactants to, preferably, 120°–180° C. It may also be carried out in a solvent, although this is not necessary. The same applies to reaction (e). A suitable group Z in both cases is halogen, preferably chlorine or bromine, although mesylates and tosylates are also useful.

Reactions (d) and (e) are preferably carried out in a dipolar aprotic solvent, e.g. acetonitrile, dimethylformamide or hexamethylphosphorotriamide, with the addition of an acid acceptor, for example anhydrous potassium carbonate or triethylamine. An additional equivalent of the amine (formula VIII, IX or X) can also be used as an acid acceptor. The reaction temperature may be from room temperature to 120° C. but is preferably from 70° to 100° C.

In processes (f) and (g), the aldehydes of the formulae XIII, XIV and XV are reacted with the amines VIII, IX and X in a condensation reaction under reductive conditions.

Suitable solvents are aliphatic and aromatic hydrocarbons, halohydrocarbons, ethers, alcohols and lower fatty acids. The reaction temperatures are from 0° to 150° C., preferably from 20° to 70° C.

Suitable reducing agents are hydrogen in the presence of a catalyst, e.g. $PtO_2$, Pd/C, nickel or cobalt catalysts, nascent hydrogen obtained from a metal and an acid, complex metal hydrides (e.g. $NaBH_4$) and hydride donors (e.g. formic acid).

If the reduction is carried out in the presence of a catalyst, atmospheric pressure is preferably employed.

The methylation of compounds of the formula X can also be effected with formaldehyde/formic acid by the Leukart/Wallach method.

The reduction of the dinitrile of the formula XVI in the presence of an alkylamine of the formula VIII, where $R^5$ may furthermore be hydrogen (reaction h and m) or of nitriles of the formulae XVII and XVIII in the presence of phenylacetonitriles of the formulae IX and X (reaction i and k) is preferably carried out as a catalytic hydrogenation using a noble metal catalyst, preferably Pd/C. Reaction temperatures are from 30° to 80° C., preferably 60° C. The reaction may be carried out under atmospheric pressure or superatmospheric pressure up to 6 bar. The solvents used are lower alcohols, acetic acid or aromatic hydrocarbons, preferably lower aliphatic alcohols, such as ethanol. From 0.1 to 10% by weight, based on the amine used, of Pd/C catalyst are required, the catalyst containing from 1 to 10% by weight of Pd on carbon.

The above reactions and the preparation of the starting materials are described in German Patent Nos. 1,154,810, 1,493,904, 1,158,083, 2,059,923 and 2,631,222, German Laid-Open Application Nos. DOS 2,263,527 and DOS 3,034,221 and European Patent Nos. 165,322, 64,148 and 47,888.

The compounds of the general formula I and their physiological addition salts with acids have useful pharmacological properties. They are highly active Ca antagonists and have a dilatory action on peripheral and central vessels and protect the brain, peripheral organs (such as the heart and kidneys) and vessels from damage due to increased Ca metabolism or Ca overloading, for example in hypoxia and ischemia. Furthermore, the compounds inhibit gastric acid secretion and have a cytoprotective and antiulcerous action. Finally, they are capable of preventing or relaxing spasms of the bronchial muscles.

In addition, these compounds have a powerful antiserotonin action. It is known that serotonin is involved in the development of spasms of central and peripheral vessels and in the thrombocyte aggregation leading to vascular occlusions and, depending on the clinical picture, may even be more important than the stimulation due to Ca ions. In such diseases, both Ca antagonists and serotonin antagonists are used. It is therefore of therapeutic value to have both active principles combined in one molecular structure.

The novel compounds are therefore suitable for the treatment of cardiovascular disorders, in particular coronary heart disease, vasospasms, cerebral ischemia, hypertension and circulatory shock. They can also be used for the prophylaxis and therapy of gastric and duodenal ulcers and asthmatic disorders.

The compounds can be administered orally or parenterally in a conventional manner. The dose depends on the age, condition and weight of the patient and on the route of administration. As a rule, the daily dose of active compound is from about 0.1 to 10 mg/kg of body weight in the case of parenteral administration. In the normal case, daily doses of from 1 to 5 mg/kg are administered orally, and from 0.05 to 0.25 mg/kg parenterally.

The level of action of the novel substances was determined by means of the following tests:

(a) Bond to the calcium channel Displacement of the specific (S)-$^3$H-devapamil bond in membrane preparations of guinea pig skeletal muscle (b) Bond to the serotonin-$S_2$-receptor Displacement of the specific $^3$H-ketanserine bond in membrane preparations of cerebral cortex of the rat Membrane homogenate was incubated for 60 minutes at room temperature with increasing concentrations (from $10^{-10}$ to $10^{-6}$M) of test substance and a fixed concentration of 1 nM of radioligand ((S)-$^3$H-devapamil or $^3$H-ketanserine). The bound and the free radioligand were separated by filtration over a glass fiber filter, and the amount of radioligand retained on the filter was determined by liquid scintillation measurement. 2 tests with 3 batches were carried out.

The competition constants ($K_i$ values in nM) were calculated by nonlinear regression analysis on an IBM computer using the program Ligand from Munson and Rodbard (Analytical Biochemistry 107 (1980), 220).

As shown in the Table, the competition constants of the novel substances in the test for calcium channel binding and serotonin-$S_2$-receptor binding are lower than those of the comparative substance verapamil. Accordingly, the affinity of the novel substances for the calcium channel is up to 14 times higher and that for the serotonin-$S_2$-receptor is up to 63 times higher.

TABLE

| Substance of Example no. | $K_i$ (nM) | |
|---|---|---|
| | (S)-$^3$H-devapamil displacement | $^3$H-ketanserine displacement |
| 1 | 16.2 | 5 |
| 2 | 19.1 | 21 |
| 4 | 5.2 | 26.4 |
| 5 | 11.9 | 20 |
| 6 | 2.9 | 11.2 |
| 10 | 9.2 | 2.8 |
| 11 | 5.8 | 10.7 |
| 13 | 3.4 | 3.3 |
| 15 | 7.5 | 6.8 |
| 16 | 34.2 | 3.6 |
| 18 | 36.7 | 4 |
| 23 | 11.6 | 48.4 |
| 24 | 8.6 | 21.1 |
| Verapamil | 41 | 177 |

The novel active compounds can be converted to the conventional pharmaceutical forms, such as tablets, coated tablets, solutions, emulsions, powders, capsules or depot forms, and to do so the conventional pharmaceutical auxiliaries and the conventional production methods may be used. Appropriate tablets can be obtained, for example, by mixing the active compounds with known auxiliaries, for example inert diluents, such as calcium carbonate, calcium phosphate or lactose, disintegrating agents, such as corn starch or alginic acid, binders, such as starch or gelatine, lubricants, such as magnesium stearate or talc, and/or agents for achieving a depot effect, such as carboxypolymethylene, carboxymethylcellulose, cellulose acetate phthalate or polyvinyl acetate.

The tablets may also consist of a plurality of layers. Coated tablets may be produced by coating cores, prepared similarly to the tablets, with agents conventionally used in tablet coatings, for example collidone or shellac, gum arabic, talc, titanium dioxide or sugar. To achieve a depot effect or to avoid incompatibility, the core may also consist of a plurality of layers. The tablet coating too may consist of a plurality of layers in order to achieve a depot effect, and the auxiliaries mentioned above in connection with the tablets may be used.

Solutions or suspensions containing the novel active compounds or active compound combinations may additionally contain sweeteners, such as saccharin, cyclamate, glycerol or sugar, and a flavor improver, for example aromas such as vanillin or orange extract.

They may also contain suspending agents or thickeners, such as sodium carboxymethylcellulose, wetting agents, for example condensates of fatty alcohols with ethylene oxide, or preservatives, such as p-hydroxybenzoates.

Injection solutions are prepared in a conventional manner, for example with the addition of preservatives, such as p-hydroxybenzoates, or stabilizers, such as Komplexones, and are introduced into injection bottles or ampoules.

Capsules containing the active compounds or active compound combinations can be prepared, for example, by mixing the active compounds with inert carriers, such as lactose or sorbitol, and encapsulating the mixture in gelatine capsules.

Suitable suppositories can be produced, for example, by mixing the active compounds or active compound combinations intended for this purpose with conventional carriers, such as neutral fats or polyethylene glycol or its derivatives.

The Examples which follow illustrate the invention without restricting it.

EXAMPLE 1

5-[N-methyl-N-(2-cyclohexyl)-ethyl]-amino-2-(3-methoxyphenyl)-2-isopropylvaleronitrile A stirred solution of 18.9 g (0.1 mole) of α-isopropyl-3-methoxyphenylacetonitrile and 21.8 g (0.1 mole) of N-(3-chloropropyl)-N-methyl-2-cyclohexylethylamine in 100 ml of toluene was heated to 85° C. 8 g (0.1 mole) of a 50% strength sodium amide suspension in toluene were then added dropwise in the course of 2 hours. The reaction solution was stirred for a further 15 minutes at 85° C. and cooled, after which 200 ml of ice water were added. The toluene phase was separated off and washed twice with water, and the toluene was then distilled off under reduced pressure. The oily residue was dissolved in 150 ml of ethanol, and a solution of hydrochloric acid in isopropanol was added. The precipitated hydrochloride was filtered off under suction and recrystallized from 200 ml of isopropanol. 34.6 g (85%) of the hydrochloride of melting point 144°–145° C. were isolated.

EXAMPLE 2

5-[N-methyl-N-(n-decyl)]-amino-2-(3,4,5-trimethoxyphenyl)-2-isopropylvaleronitrile 41.9 g (0.1 mole) of 5-[N-methyl-N-(n-decyl)]-amino-2-(3,4,5-trimethoxyphenyl)-valeronitrile were dissolved in 200 ml of toluene, and the stirred solution was refluxed with 4.7 g (0.12 mole) of powdered sodium amide for 1 hour. A solution of 15.7 g (0.12 mole) of isopropyl bromide in 30 ml of toluene was then added dropwise in the course of 60 minutes, and the mixture was refluxed for a further 2 hours. The cooled reaction mixture was poured into water, the toluene phase was washed several times with water and the toluene was then distilled off. The residue was dissolved in 100 ml of isopropanol, and ethanolic hydrochloric acid was added. The hydrochloride was filtered off under suction and then recrystallized from ethanol. 45.7 g (92%) of the hydrochoride of melting point 116°–117° C. were isolated.

EXAMPLE 3

5-[N-methyl-N-(n-octyl)]-amino-2-phenyl-2-isopropylvaleronitrile 11.7 g (0.1 mole) of phenylacetonitrile were dissolved in 15 ml of toluene, and 52 g (0.8 mole) of 85% pure potassium hydroxide powder and 0.2 g of tris-(3,6-dioxaheptyl)-amine was added. 12.3 g of isopropyl bromide were then added dropwise to the stirred mixture at a rate such that the reaction temperature did not exceed 50° C. When the addition was complete, stirring was continued for a further 30 minutes at 50° C., after which a solution of 22.0 g (0.1 mole) of N-(3-chloropropyl)-N-methyloctylamine in 200 ml of toluene was added at 90° C. The reaction mixture was stirred for a further 3 hours at 90° C. and cooled, 100 ml of water were added and the toluene phase was then separated off. The toluene was distilled off to give a yellow oil, which was chromatographed over a silica gel column using a solvent mixture consisting of methylene chloride/acetone/methanol in a ratio of 9:1:0.5. 24.0 g of the base were isolated.

| Analysis: | Calculated | C 80.6 | H 11.2 | N 8.2 |
|---|---|---|---|---|
| | Found | C 80.5 | H 11.1 | N 8.2 |

EXAMPLE 4

5-[N-methyl-N-(n-octyl)]-amino-2-(3,4,5-trimethoxyphenyl)-2-isopropylvaleronitrile 41.9 g (0.1 mole) of 5-[N-(n-octyl)]-amino-2(3,4,5-trimethoxyphenyl)-2-isopropylvaleronitrile were dissolved in 50 ml of formic acid at room temperature, 11.9 ml of 35% strength aqueous formalin solution (0.15 mole) were added and the mixture was heated on a water bath until evolution of carbon dioxide had ceased. After cooling, the reaction solution was diluted with water and rendered alkaline by adding ammonia, and the base which had separated out was extracted with ether. The ether solution was washed several times with water and dried with potassium carbonate. The ether was then distilled off. The residue was chromatographed over a silica gel column and then converted to the hydrochloride. 43.2 g (92%) of a product of melting point 169°–171° C. were obtained.

EXAMPLE 5

5-[N-methyl-N-(2-cyclohexyl)-ethyl]-amino-2-(3,5-diethoxyphenyl)-2-isopropylvaleronitrile 32.4 g (0.1 mole) of α-isopropyl-α-(3-chloropropyl)-3,5-diethoxyphenylacetonitrile were dissolved in 45 ml of hexamethylphosphorotriamide, and 30 g of powdered anhydrous potassium carbonate were added. The reaction mixture was heated for 4 hours at 80° C. and cooled, after which 500 ml of water were added and the mixture was extracted twice with ether. The ether phase was washed several times with water and dried over potassium carbonate, and the ether was distilled off. The resulting crude base was purified by chromatography. 32.2 g (75%) of base were isolated.

| Analysis: | Calculated | C 75.6 | H 10.3 | N 6.5 |
|---|---|---|---|---|
| | Found | C 75.5 | H 10.1 | N 6.6 |

EXAMPLE 6

(S)-5-[N-methyl-N-(n-octyl)]-amino-2-(3,4,5-trimethoxyphenyl)-2-isopropylvaleronitrile 38.5 g (0.1 mole) of (S)-α-isopropyl-α-(3-methanesulfonyloxypropyl)-3,4,5-trimethoxyphenylacetonitrile (mp. 101° C., $[\alpha]_D^{20}=20°$, c=10 mg/ml, ethanol, d=10 cm), 31.5 g of N-methyloctylamine and 0.5 g of tetrabutylammonium bromide in 100 ml of acetonitrile were heated at 60° C. for 2.5 hours. After cooling, the reaction mixture was poured into 200 ml of water and extracted with twice 150 ml of n-hexane. The n-hexane phase was washed several times with aqueous sodium chloride solution and dried with potassium carbonate, after which the n-hexane was distilled off. The crude base was dissolved in a 3:2 ether/diisopropyl ether mixture, and ethanolic hydrochloric acid was added until the pH was slightly acidic. 33.8 g (78%) of the hydrochloride of melting point 131°–133° C., $[\alpha]_{589}^{20}= -8.7°$ (c=10 mg/ml, ethanol, d=10 cm), were isolated.

EXAMPLE 7

(R)-5-[N-methyl-N-(n-octyl)]-amino-2-(3,4,5-trimethoxyphenyl)-2-isopropylvaleronitrile The dextrorotatory antipode was obtained in the form of the hydrochloride of melting point 131°–133° C., $[\alpha]_{589}^{20}= +8.8°$ (c=10 mg/ml, ethanol, d=10 cm), from 32.6 g (0.1 mole) of (R)-α-isopropyl-α-(3-chloropropyl)-3,4,5-trimethoxyphenylacetonitrile (German Patent No. 2,059,985) and 14.3 g (0.1 mole) of N-methyloctylamine using a method similar to that described in Example 5.

EXAMPLE 8

5-[N-(2-cyclohexyl)-ethyl]-amino-2-(3,5-diethoxyphenyl)-2-isopropylvaleronitrile 30.4 g (0.1 mole) of 5-amino-2-(3,5-diethoxyphenyl)-2-isopropylvaleronitrile and 19.1 g (0.1 mole) of 2-bromoethylcyclohexane gave, after chromatographic purification of the product, 25.7 g (62%) of the base, the procedure used being similar to that described in Example 5.

| Analysis: | Calculated | C 75.3 | H 10.2 | N 6.8 |
|---|---|---|---|---|
| | Found | C 75.4 | H 10.0 | N 6.7 |

EXAMPLE 9

5-[N-methyl-N-(2-cyclohexyl)ethyl]-amino-2-phenyl-2-isopropylvaleronitrile 21.5 g (0.1 mole) of 4-phenyl-4-cyano-5-methylhexanal and 14.1 g (0.1 mole) of N-methyl-2-cyclohexylethylamine were dissolved in 100 ml of toluene. 4.6 g (0.1 mole) of formic acid were added at room temperature. The reaction mixture was refluxed until the evolution of gas had died down. Aqueous potassium carbonate solution was added to the cooled reaction solution, the liberated amine was extracted with ether, the ether phase was washed several times with water and dried, the ether was distilled off and the oily base was then dissolved in isopropanol and ethanolic hydrochloric acid was added. Recrystallization from isopropanol gave 34.7 g of the hydrochloride of melting point 142°-144° C.

EXAMPLE 10

5-[N-methyl-N-(2-cyclohexyl)-ethyl]-amino-2-(3,5-dimethoxyphenyl)-2-isopropylvaleronitrile A mixture of 29.0 g (0.1 mole) of 2-(3,5-dimethoxyphenyl)-2-isopropyl-5-methylaminovaleronitrile (prepared by catalytic hydrogenation of 2-(3,5-dimethoxyphenyl)-2-isopropyl-1,3-dicyanopropane) and 12.6 g of cyclohexylacetaldehyde was catalytically reduced with 400 mg of 5% strength palladium on carbon in 100 ml of toluene under atmosphere pressure at from 25° to 30° C. in the course of 10 hours. After the catalyst had been removed, the toluene solution was washed several times with water and dried with potassium carbonate. The toluene was then distilled off. The residue was purified by column chromatography. 32.1 g (80%) of colorless base were isolated.

| Analysis: | Calculated | C 75.0 | H 10.1 | N 7.0 |
|---|---|---|---|---|
| | Found | C 75.3 | H 10.1 | N 7.1 |

EXAMPLE 11

5-[N-methyl-N-(2-cyclohexyl)-ethyl]-amino-2-(3,4,5-trimethoxyphenyl)-2-isopropylvaleronitrile In a hydrogenation apparatus, 30.2 g of 2-(3,4,5-trimethoxyphenyl)-2-isopropyl-1,3-dicyanopropane were dissolved in 150 ml of isopropanol, 4 g of 5% strength Pd/C were added and the apparatus was flushed with nitrogen. 2 ml of aqueous cetyltrimethylammonium chloride solution were added, after which a stream of hydrogen was passed through the apparatus with vigorous stirring, and the stock vessel was filled with hydrogen. 14.1 g (0.1 mole) of N-methyl-2-cyclohexylethylamine were then added to the reaction mixture, and hydrogenation was carried out at from 50° to 60° C. under a slight excess pressure of hydrogen. The hydrogenation was complete after 2 hours. The catalyst was separated off, the isopropanol was distilled off, the residue was taken up in ethyl acetate and ethanolic hydrochloric acid was added. 39.7 g (85%) of the hydrochloride of melting point 171°-173° C. were isolated.

EXAMPLE 12

5-[N-(2-cyclohexyl)ethyl]-amino-2-(3,4,5-trimethoxyphenyl)-2-isopropylvaleronitrile 35.4 g (85%) of the base were obtained from 30.6 g (0.1 mole) of 5-amino-2-(3,4,5-trimethoxyphenyl)-2-isopropylvaleronitrile and 12.3 g (0.1 mole.) of cyclohexylacetonitrile by a method similar to that described in Example 11, the said base being purified by column chromatography.

| Analysis: | Calculated | C 72.1 | H 9.7 | N 6.7 |
|---|---|---|---|---|
| | Found | C 72.0 | H 9.8 | N 6.8 |

The following were obtained in a similar manner:

(13) (S)-5-[N-methyl-N-(2-cyclohexyl)-ethyl]-amino-2-(3,4,5-trimethoxyphenyl)-2-isopropylvaleronitrile hydrochloride mp. 175°-176° C., $[\alpha]_{589}^{20} = -9.5°$ (c=10 mg/ml, ethanol, d=10 cm).

(14) (R)-5-[N-methyl-N-(2-cyclohexyl)ethyl]-amino-2-(3,4,5-trimethoxyphenyl)-2-isopropylvaleronitrile hydrochloride mp. 175°-176°, $[\alpha]_{589}^{20} = +9.1°$ (c=10 mg/ml, ethanol, d=10 cm).

(15) 5-[N-methyl-N-(n-octen-3-yl)]-amino-2-(3,4,5-trimethoxyphenyl)-2-isopropylvaleronitrile hydrochloride m.p 176° C.

(16) 5-[N-methyl-N-(2-cyclohexyl)ethyl]-amino-2-(2-nitro-3,4-dimethoxyphenyl)-2-isopropylvaleronitrile

| Analysis: | Calculated | C 67.4 | H 8.8 | N 9.4 |
|---|---|---|---|---|
| | Found | C 67.5 | H 8.7 | N 9.4 |

(17) 5-[N-methyl-N-(2-cyclohexyl)ethyl]-amino-2-(4-nitro-3,5-dimethoxyphenyl)-2-isopropylvaleronitrile

| Analysis: | Calculated | C 67.4 | H 8.8 | N 9.4 |
|---|---|---|---|---|
| | Found | C 67.2 | H 8.8 | N 9.3 |

(18) 5-(N-methyl-N-[2-(cyclohexen-1-yl)ethyl]}-amino-2-phenyl-2-isopropylvaleronitrile.

| Analysis: | Calculated | C 81.6 | H 10.1 | N 8.3 |
|---|---|---|---|---|
| | Found | C 81.8 | H 9.8 | N 8.4 |

(19) 5-[N-methyl-N-(2-cyclohexyl)ethyl]-amino-2-(3,4-dimethoxyphenyl)-2-isopropylvaleronitrile hydrochloride, mp. 131°-132° C.

(20) 5-{N-methyl-N-[2-(cyclohexen-1-yl)ethyl]}-amino-2-(3,4,5-trimethoxyphenyl)-2-isopropylvaleronitrile hydrochloride, mp. 165°-167° C.

(21) 5-{N-methyl-N-[2-(cyclohexen-1-yl)ethyl]}-amino-2-(3,4-dimethoxyphenyl)-2-isopropylvaleronitrile

| Analysis: | Calculated | C 75.3 | H 9.6 | N 7.0 |
|---|---|---|---|---|
| | Found | C 75.2 | H 8.9 | N 7.0 |

(22) 5-[N-methyl-N-(n-nonyl)]-amino-2-(3,4,5-trimethoxyphenyl)-2-isopropylvaleronitrile hydrochloride, mp. 142°-143° C.

(23) 5-[N-methyl-N-(n-hexyl)]-amino-2-(3,4,5-trimethoxyphenyl)-2-isopropylvaleronitrile hydrochloride, mp. 150°-152° C.

(24) (S)-5-[N-methyl-N-(n-hexyl)]-amino-2-(3,4,5-trimethoxyphenyl)-2-isopropylvaleronitrile hydrochloride, mp. 143°-145° C., $[\alpha]_{589}^{20} = -9.0°$ (c=10 mg/ml, ethanol, d=10 cm).

(25) (R)-5-[N-methyl-N-(n-hexyl)]-amino-2-(3,4,5-trimethoxyphenyl)-2-isopropylvaleronitrile hydrochloride, mp. 143°-145° C., $[\alpha]_{589}^{20} = -9.0°$ C. (c=10 mg/ml, ethanol, d=10 cm).

(26) (S)-5-[N-methyl-N-(2-cyclohexylethyl)]-amino-2-phenyl-2-isopropylvaleronitrile hydrochloride, mp. 180°-183° C., $[\alpha]_{589}^{20} = -9.4°$, (c=10 mg/ml, ethanol, d=10 cm).

(27) (R)-5-[N-methyl-N-(2-cyclohexylethyl)]-amino-2-phenyl-2-isopropylvaleronitrile hydrochloride, mp. 180°-183° C., $[\alpha]_{589}^{20} = -9.4°$, (c=10 mg/ml, ethanol, d=10 cm).

(28) 5-{N-[2-(cyclohexen-1-yl)ethyl]}-amino-2-isopropyl-2-phenylvaleronitrile hydrochloride, mp. 180°-182° C.

(29) 5-[N-2-(cyclohexyl)ethyl-N-methyl]-amino-2,2-diphenylvaleronitrile hydrochloride, mp. 82°–84° C.

(30) 5-[N-2-(cyclohexyl)ethyl-N-methyl]-amino-2-(cyclohexen-1-yl)-2-phenylvaleronitrile hydrochloride, mp. 150°–152° C.

The following can be prepared in a similar manner:

4-[N-methyl-N-(n-octyl)]-amino-2-(3,5-dimethoxyphenyl)-2-isopropylbutryonitrile, 6-[N-(n-heptyl)-N-methyl]-amino-2-(n-propyl)-2-(3,4,5-trimethoxyphenyl)-capronitrile, 5-[N-(n-butyl)-N-(n-hexyl)]-amino-2-isopropyl-2-(3-methoxyphenyl)valeronitrile, 5-(N-ethyl-N-(n-undecyl)-amino-2-isopropyl-2-(3,4,5-trimethoxy-phenyl)valeronitrile, 5-[N-(2-cyclohexyl)ethyl-N-methyl]-amino-2-isopropyl-2(3-trifluoromethylphenyl)-valeronitrile, 5-[N-(n-dodecyl)-N-methyl]-amino-2-(4-chlorophenyl)-2-allylvaleronitrile, 5-[N-(2-cyclohexyl)ethyl-N-methyl]-amino-2-(3-fluorophenyl)-2-isopropylvaleronitrile, 5-[N-methyl-N-(n-octyl)]-amino-2-isopropyl-2-(m-tolyl)-valeronitrile, 5-[N-methyl-N-(n-nonyl)]-amino-2-(4-ethylphenyl)-2-isopropylvaleronitrile, 5-[N-(2-cyclohexyl)ethyl-N-methyl]-amino-2-(4-tert-butylphenyl)-2-isopropylvaleronitrile, 5-[N-methyl-N-(n-octyl)]-amino-2-isopropyl-2-(1,2,3,4-tetrahydro-naphthyl-2)-valeronitrile, 5-[N-(2-cyclohexyl)ethyl-N-methyl]-amino-2-isopropyl-2(3,4-methylenedioxyphenyl)-valeronitrile, 5-[N-methyl-N-(n-hexyl)]-amino-2-(1,3-benzodioxan-6-yl)-2-isopropylvaleronitrile, 5-[N-ethyl-N-(n-octyl)]-amino-2-(1,4-benzodioxan-6-yl)-2-isopropylvaleronitrile

EXAMPLE A

Tablets having the following composition are prepared in a conventional manner on a tablet press:
40 mg of the substance of Example 11
120 mg of corn starch
13.5 mg of gelatine
45 mg of lactose
2 25 mg of Aerosil ® (chemically pure silica in the form of submicroscopic particles)
6.75 mg of potato starch (as a 6% strength paste).

EXAMPLE B

Coated tablets having the following composition are prepared in a conventional manner:
20 mg of the substance of Example 11
60 mg of core material
60 mg of sugar-coating material The core material consists of 9 parts of corn starch, 3 parts of lactose and 1 part of Luviskol ® VA 64 (60:40 vinylpyrrolidone/vinylacetate copolymer, cf. Pharm. Ind. 1962, 586). The sugar-coating material consists of 5 parts of sucrose, 2 parts of corn starch, 2 parts of calcium carbonate and 1 part of talc. The coated tablets prepared in this manner are then provided with a coating resistant to gastric juice.

EXAMPLE C 10 g of the substance of Example 11 are dissolved in 5,000 ml of water with the addition of NaCl, and the solution is brought to pH 6.0 with 0.1 N NaOH so that a blood-isotonic solution is formed. 5 ml portions of this solution are introduced into ampoules and sterilised.

We claim:

1. A basically substituted phenylacetonitrile of the formula

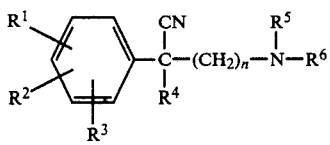

where
$R^1$, $R^2$ and $R^3$ are identical or different and are each hydrogen, halogen, trifluoromethyl, $C_1$–$C_4$-alkyl, nitro or $C_1$–$C_4$-alkoxy, and two of the radicals $R^1$, $R^2$ and $R^3$ in adjacent positions may furthermore together form a methylenedioxy, ethylenedioxy, 1,3-dioxatetramethylene, propylene or butylene group,
$R^4$ is a saturated or unsaturated alkyl or cycloalkyl group of not more than 8 carbon atoms or phenyl,
$R^5$ is hydrogen or $C_1$–$C_4$-alkyl,
$R^6$ is a saturated or unsaturated hydrocarbon radical of 6 to 15 carbon atoms which may contain a non-aromatic ring, and
n is 2, 3 or 4, antipodes and physiologically tolerated acid addition salts thereof.

2. The phenylacetonitrile of claim 1 in which said hydrocarbon radical contains a ring.

3. The phenylacetonitrile of claim 2 in which said ring is a cyclohexyl or a cyclohexen-1-yl ring.

4. A therapeutic composition useful in the treatment of cardiovascular disorders, asthmatic disorders and peptic ulcers comprising a pharmaceutically acceptable carrier and an effective amount of a basically substituted phenylacetonitrile of the formula

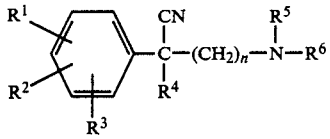

where
$R^1$, $R^2$ and $R^3$ are identical or different and are each hydrogen, halogen, trifluoromethyl, $C_1$–$C_4$-alkyl, nitro or $C_1$–$C_4$-alkoxy and two of the radicals $R^1$, $R^2$ and $R^3$ in adjacent positions may furthermore together form a methylenedioxy, ethylenedioxy, 1,3-dioxatetramethylene, propylene or butylene group,
$R^4$ is a saturated or unsaturated alkyl or cycloalkyl group of not more than 8 carbon atoms or phenyl,
$R^5$ is hydrogen or $C_1$–$C_4$-alkyl,
$R^6$ is a saturated or unsaturated hydrocarbon radical of 6 to 15 carbon atoms which may contain a non-aromatic ring, and
n is 2, 3 or 4, antipodes and physiologically tolerated acid addition salts thereof as the active compound.

5. The composition of claim 4 in which said hydrocarbon radical contains a ring.

6. The composition of claim 5 in which said ring is a cyclohexyl or a cyclohexen-1-yl ring.

7. 5-[N-methyl-N-(n-octyl)]-amino-2-(3,4,5-trimethoxyphenyl)-2-isopropylvaleronitrile and its enantiomers.

8. 5-[N-methyl-N-(n-hexyl)]-amino-2-(3,4,5-trimethoxyphenyl)-2-isopropylvaleronitrile and its enantiomers.

9. 5-[N-methyl-N-(2-cyclohexyl)ethyl]-amino-2-(3,4,5-trimethoxyphenyl)-2-isopropylvaleronitrile and its enantiomers.

10. 5-[N-methyl-N-(2-cyclohexyl)ethyl]-amino-2-phenyl-2-isopropylvaleronitrile and its enantiomers.

11. 5-{N-methyl-N-[2-(cyclohexen-1-yl)ethyl]}-amino-2-(3,4,5-trimethoxyphenyl)-2-isopropylvaleronitrile and its enantiomers.

12. 5-{N-methyl-N-[2-(cyclohexen-1-yl)ethyl]}-amino-2-phenyl-2-isopropylvaleronitrile and its enantiomers.

13. The method of treating cardiovascular diseases, asthmatic disorders or peptic ulcers in a patient suffering therefrom, which comprises administering to said patient an effective amount of a basically substituted phenylacetonitrile of the formula

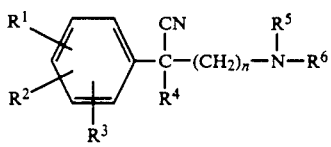

where
$R^1$, $R^2$ and $R^3$ are identical or different and are each hydrogen, halogen, trifluoromethyl, $C_1$-$C_4$-alkyl, nitro or $C_1$-$C_4$-alkoxy, and two of the radicals $R^1$, $R^2$ and $R^3$ in adjacent positions may furthermore together form a methylenedioxy, ethylenedioxy, 1,3-dioxatetramethylene, propylene or butylene group,
$R^4$ is a saturated or unsaturated alkyl or cycloalkyl group of not more than 8 carbon atoms or phenyl,
$R^5$ is hydrogen or $C_1$-$C_4$-alkyl,
$R^6$ is a saturated or unsaturated hydrocarbon radical of 6 to 15 carbon atoms which may contain a non-aromatic ring, and
n is 2, 3 or 4, antipode and physiologically tolerated acid addition salts thereof.

14. The method of claim 13, in which said hydrocarbon radical contains a ring.

15. The method of claim 14, in which said ring is a cyclohexyl or a cyclohexen-1-yl ring.

* * * * *

UNITED STATES PATENT AND TRADEMARK OFFICE
CERTIFICATE OF CORRECTION

PATENT NO. : 4,940,780
DATED : July 10, 1990
INVENTOR(S) : SEITZ et al.

It is certified that error appears in the above-identified patent and that said Letters Patent is hereby corrected as shown below:

ON THE TITLE PAGE:

Inventor "Ruebsmen" should read --Ruebsamen--

IN THE ABSTRACT

Last line, "disorders" should read --cardiovascular diseases, asthmatic disorders or peptic ulcers in a patient--

In the formula in the abstract, after "C" abd before the "(" insert a -- - --.

IN THE CLAIMS

Claims 4 and 13, line 21, "and" should read --or--

Signed and Sealed this

Eighth Day of October, 1991

Attest:

HARRY F. MANBECK, JR.

*Attesting Officer*    *Commissioner of Patents and Trademarks*